United States Patent [19]

Balassa

[11] Patent Number: 4,665,993

[45] Date of Patent: May 19, 1987

[54] HYDRATED FIBROUS MATS

[76] Inventor: Leslie L. Balassa, Shore Dr., Blooming Grove, N.Y. 10914

[21] Appl. No.: 744,119

[22] Filed: Jun. 12, 1985

[51] Int. Cl.[4] ............................................... A62C 1/02
[52] U.S. Cl. ...................................... 169/44; 169/47; 252/2
[58] Field of Search .................. 169/44, 46, 47, 50, 169/48, 66; 162/99, 57, 4, 147, 97, 96, 159; 252/607, 2, 601

[56] References Cited

U.S. PATENT DOCUMENTS

| | | | |
|---|---|---|---|
| 1,199,241 | 10/1916 | Burton | 162/57 |
| 1,718,012 | 6/1929 | Vogt et al. | 162/99 X |
| 1,828,243 | 10/1931 | Darling | 162/99 X |
| 2,068,151 | 1/1937 | Remler | 162/97 X |
| 2,849,316 | 8/1958 | Lauring | 162/159 |
| 3,759,330 | 9/1973 | Rainey et al. | 169/47 |
| 3,884,750 | 5/1975 | Iannazzi | 162/2 |
| 4,012,561 | 3/1977 | Doughty et al. | 162/147 |
| 4,278,552 | 7/1981 | Hisamoto et al. | 169/47 |

Primary Examiner—Jeffrey V. Nase
Attorney, Agent, or Firm—Darby & Darby

[57] ABSTRACT

Disclosed is a hydrated fibrous mass prepared by the steps including introducing a source of cellulosic fibers to water with continuous mixing until a ratio of water to fibers of about 50 to 1 is obtained and mixing the water and source of cellulosic fibers until the source of cellulosic fibers has been comminuted to substantially individual cellulose fibers. The mass can be effectively used as a fire controlling agents. The mass can also be used as a carrier for pesticides, and as a concrete or cement cure rate controlling agent.

5 Claims, 1 Drawing Figure

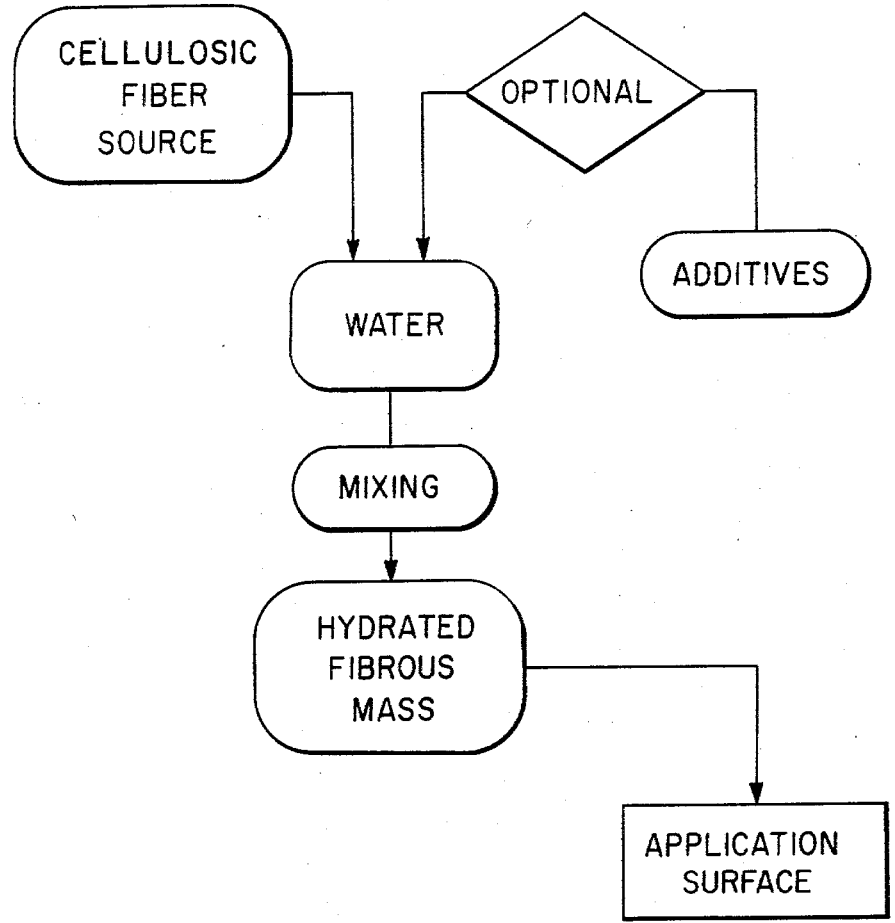

HYDRATED FIBROUS MATS

FIELD OF THE INVENTION

The present invention relates to the preparation and use of a hydrated fibrous mass consisting of a slurry of cellulosic fibers swollen with water. More particularly, the present invention relates to the use of such a mass in firefighting, agricultural applications and in other applications where it is desirable to efficiently and economically apply large amounts of water to a large surface area without rapid dissipation or evaporation.

BACKGROUND OF THE INVENTION

In firefighting, water has certain disadvantages which reduce its efficacy in extinguishing fires. The primary effect of water on fire is cooling, thereby reducing the ability of the fuel to burn, and displacement of oxygen necessary for the combustion of fuel. Unfortunately, water has a relatively high surface tension with attendant poor wetting properties for many surfaces. Water also has a low viscosity and flows well at any temperature between its freezing and boiling points. When water is brought into contact with very hot surfaces it has a tendency to bead and roll off the surface. This phenomenon is caused by the formation of a layer of steam between the surface and the water which acts to insulate the water from direct contact with the hot surface, reducing the ability of the water to absorb heat from the surface or displace oxygen.

Additives can be introduced to water used for firefighting to reduce the inherent disadvantages of water as a fire extinguishing agent. Surfactants can be added to water to improve its wetting properties. Gelling agents can be added to water to form a gel for use as a firefighting agent. Such gels, however, lose cohesion and viscos - on contact with hot surfaces. Foaming agents combined with water can be quite effective in smothering fires under special conditions. However, foams cannot be used in large fires since high winds created by major fires dissipate the foam or prevent its accurate application. In addition, in the case of chemical fires, burning chemicals frequently cause the collapse of the foam and consequent loss of most of its fire extinguishing properties.

OBJECT OF THE INVENTION

It is an object of the present invention to provide a hydrated mat of fibers, capable of retaining large quantities of water for application to large surface areas where it is desirable to accurately direct large amounts of water economically and efficiently and to retain water on the surface area without rapid dissipation or evaporation.

SUMMARY OF THE INVENTION

It has now been unexpectedly discovered that a hydrated mass of cellulosic fibers can be effectively used to extinguish fires and especially wood burning conflagrations. A hydrated fibrous mass can also be used as a carrier for pesticides and as a concrete or cement cure rate controlling agent.

The hydrated mass is prepared by the steps including introducing a source of cellulosic fibers to water with continuous mixing until a ratio of water to fibers of about 50 to 1 is obtained, and mixing the water and source of cellulosic fibers until the source of cellulosic fibers has been comminuted to substantially individual cellulose fibers.

DESCRIPTION OF THE INVENTION

The object of the invention is met by providing a hydrated mass of fibers comprising water retained in a carrier of cellulosic fibers. It is well known that cellulose fibers absorb several times their weight in water and a mass of such fibers is capable of retaining additional water immobilized by cohesion. A fibrous mat formed from a mass of cellulose fibers and water forms an inexpensive, nonflowing wet blanket.

Depending on the desired application, the characteristics of the fibrous mass can be determined by the type of cellulose fibers selected, the length of the fibers used, the pH of the water retained by the fibrous mass, and by chemical additives to the water which can enhance various characteristics of the hydrated fibrous mass.

Any cellulosic fiber can be used as the carrier to form the fibrous mass provided that the material must be capable of being shredded, beaten or pulped into fibers which are capable of swelling in water and forming a fibrous mat. Preferred fiber diameters are from 0.1 to 0.8 mm (millimeters). Preferred fiber length is from 2 to 10 mm. Shredded newsprint is the preferred source of cellulosic fibers. Newsprint is readily available in virtually unlimited quantities at low cost and is bio-degradable and therefore ecologically acceptable for use in fighting brush or grass fires for example, or for use in agricultural applications. Other types of materials from which cellulosic fibers can be obtained include wood pulp, shredded corn cob, straw, leaves and other types of cellulosic biomass. Well-known chemical additives can be introduced to water used in forming the mass to assist in causing swelling of the cellulosic fibers. Urea, sodium hydroxide and potassium hydroxide are examples of such additives. Swelling is a function of the capacity of the fiber to absorb water, but not all absorbing fibers will swell and retain water. Nonabsorbing fibers do not retain water except for retention due to cohesion. FIG. 1 shows a flow diagram of the method of the present invention, including the steps for preparing the hydrated fibrous mass, and the application of the mass to an application surface.

In order to illustrate the present invention, reference is made to the following examples which are not intended to limit the invention in any respect.

EXAMPLE 1

A hydrated fibrous mass was prepared by introducing 1,000 ml (milliliters) of water having a pH of 6 to a Vita Mix Model 3600 mixer from Vita-Mix Corp., Cleveland, Ohio. 55 grams of shredded newsprint having 5% moisture content were introduced to the mixer while the mixer was running at low speed (150 rpm) (revolutions per minute). The newsprint was gradually introduced over a period of 5 minutes. After all of the newsprint had been added to the mixer, the speed of the mixer was increased to about 3000 rpm. After five minutes of mixing at 3000 rpm, a homogeneous non-flowing mass was obtained. The viscosity of the mass was determined to be approximately 500 cps (centipoise). On horizontal surfaces the hydrated fibrous mat can be built up to a thickness of 4 to 6 centimeters. On vertical surfaces, the mat can be applied in thicknesses of up to 0.5 to 1.0 centimeters.

Providing water with an alkaline pH aids in disintegrating the newsprint into individual cellulose fibers.

The hydrated fibrous mass of Example 1 can be used to quickly extinguish brush or grass fires, as well as industrial or structure fires, by blanketing the area affected with the hydrated fibrous mass to form a fibrous mat on the ground. Due to the density and viscosity of the fibrous mass, the mass will remain in contact even with inclined surfaces (such as burning trees). The fibrous mass can also be used to prevent the spreading of a fire by covering forest floor litter and brush.

An acidic pH is not preferred unless an acidic swelling agent such as phosphoric acid ($H_3PO_4$) is being used.

The hydrated fibrous mass of the present invention should not be used to extinguish fires where water is contra-indicated. Such fires include electricity and machinery fires as well as certain types of chemical fires.

The fibrous mass can be prepared ahead of time and then transported to the scene of a fire. The mass can be stored in containers of convenient size and weight. Paper or plastic bags of 25 to 100 pound capacity are acceptable. The prepared mass can then be transported by air to the scene of a fire and then ejected from a plane or other aircraft onto the fire. Alternatively, the mass can be prepared from separate water and fibers onboard an aircraft, for example, and then ejected onto a fire. Depending on fiber content, the mass can be applied by spraying through nozzles (fiber content of 2–5%), thrown by rotating throw wheels or dropped from the air by plane or other aircraft (fiber content of 5–10%).

EXAMPLE 2

A hydrated fibrous mass of high viscosity was prepared by introducing 1,000 liters of tap water at pH 5.5 to a Cowles-type disperser (obtained from Myers Engineering, Bell, California) having a 30 centimeter blade, a 20 horsepower motor, and a capacity of 1,000 liters. The water was introduced to the disperser and the mixer was operated at 200 rpm. 100 kilograms of shredded newsprint having a 5% moisture content were added to the mixer as in Example 1, with the disperser mixing at approximately 200 rpm. After the introduction of the newsprint, the speed of the disperser was increased to approximately 750–1000 rpm and mixing continued until a homogeneous dispersion was obtained (after approximately 15 minutes).

The material obtained is non-flowing, having a viscosity of approximately 1000 cps, and may be built up to about 10 centimeters thickness on a horizontal surface. A hydrated mass of this viscosity is of particular value in protecting buildings in city fires, for example, by blanketing the roof of a building, thereby preventing sparks and cinders being emitted from a burning building from igniting adjacent buildings.

In certain applications it is desirable to provide the hydrated mass with additives which act as fire retarding agents. For example, in large-scale fires wherein high temperatures in excess of 1500° F. are encountered for more than one hour, the hydrated mass may be heated for such a duration that the retained water is evaporated, leaving dried cellulose fibers. To prevent these fibers from becoming fuel for the fire sought to be extinguished, flame retardant agents can be employed as adjuvants. These agents may be dissolved in the water introduced to the mixer prior to the addition of shredded newsprint or other sources of cellulosic fibers. Flame retardant agents which can be used include the following:

| | |
|---|---|
| Tri-sodium phosphate | 0.5 to 10% of dry fiber weight |
| Borax | 1.0 to 5% of dry fiber weight |
| Urea | 1.0 to 20% of dry fiber weight |
| Sodium Silicate | 5.0 to 20% of dry fiber weight |

These agents act to prevent the dried fibers from becoming a fuel source by absorbing or adsorbing onto the fiber and causing the fiber to char without flame and without forming glowing embers.

Anionic surfactants can be added to the hydrated fibrous mass to increase the wetting properties of the mass. Suitable surfactants for use in the invention include glyceryl monooleate, sodium lauryl sulfate, and lignin sulfonate, among others. A preferred surfactant is sodium lauryl sulfate added in an amount from about 0.1 to 0.6% by weight of the dispersion. Higher proportions of surfactants such as sodium lauryl sulfate are undesirable because incorporation of air and foaming of the fiber dispersion will occur. Such foaming will reduce the weight to volume ratio of the hydrated fibrous mass reducing its overall effectiveness.

Additives can be introduced to the hydrated fibrous mass to increase the viscosity and therefore the cohesion and clinging properties of the hydrated fibrous mass. The following additives are preferred for use in the present invention: Methylcellulose added at 1.0 to 4.0% by weight of the dispersion; carboxymethlycellulose added at between 1.0 to 4.0% by weight of the dispersion; sodium silicate added at 3.0 to 15% by weight of the dispersion; and sodium alginate added at 1.0 to 10% by weight of the dispersion. These viscosity enhancers should be dissolved in water (with mixing) before the addition of the cellulosic fiber source.

Various bio-mass sources of cellulosic fibers can be used to provide the hydrated fibrous mass of the present invention. Such materials include corn cobs, corn stalks, straw, cane, dry leaves, and cardboard. Urea (at 10–20% by weight of the dispersion) or sodium hydroxide (at 5–15% by weight of the dispersion) can provide the required degree of swelling. Depending on the cellulosic fiber source, fiber swelling should be between about 10–200%.

In addition to serving as a useful firefighting aid, the hydrated fibrous mass of the present invention can be used in agricultural applications. The mass may be spread on to the soil surface at a thickness necessary to supply moisture to the soil and to release water over a period of time while keeping it near the surface. If the material is to be applied to a dry, water-repellent surface, the addition of a surfactant to the mass will overcome the initial repellency of the soil surface. Suitable surfactants for use in the invention include glyceryl monooleate, sodium lauryl sulfate and lignin sulfonate, among others.

The hydrated mass of the present invention can also be used as a carrier for fertilizers, herbicides or pesticides. The aerial application of herbicides and pesticides can be made more efficient by reducing loss through wind drift by incorporating the pesticides or herbicides into the mass of the present invention and then applying the mass to the desired location. The pesticides which can be employed as adjuvants to the hydrated fiber mass include any water soluble or water dispersible herbicide or insecticide such as diazinone and ammonium sulfonate, among others.

The hydrated fibrous mass of the present invention can also be used to control the rate of cure of fresh cement or concrete by applying the mass to the surface of the fresh cement or concrete at a desired thickness to form a hydrated mat. After the cement or concrete has cured properly, the fibrous residue of the hydrated mat can be easily removed by sweeping or vacuuming.

What is claimed is:

1. A method of extinguishing a first comprising the steps of:
   preparing a hydrated fibrous mass by the steps including introducing a source of cellulosic fibers to water with continuous mixing until a ratio of water to fibers of from between about 10 to 1 and about 50 to 1 is obtained, and mixing the water and source of cellulosic fibers until until the source of cellulosic fibers has been comminuted to substantially individual cellulose fibers; and
   applying said mass to an area where said fire is to be extinguished.

2. The method of claim 1 further comprising a viscosity enhancer selected from the group consisting of methylcellulose, carboxymethylcellulose, sodium silicate, and sodium alginate.

3. The method of claim 1 wherein said mass is aerially applied to said area.

4. The method of claim 1 wherein said source of cellulosic fibers is selected from the group consisting of newsprint, corn cobs, corn stalks, straw, cane, dry leaves and cardboard.

5. A method of extinguishing a fire comprising the step of:
   preparing a hydrated fibrous mass by the steps including introducing a source of cellulosic fibers to water with continuous mixing until a ratio of water to fibers of from between about 10 to 1 and about 50 to 1 is obtained, and mixing the water and source of cellulosic fibers until the source of cellulosic fibers has been comminuted to substantially individual cellulose fibers, and introducing to said mass a flame retardant agent selected from the group consisting of tri-sodium phophate, borax, urea, sodium silicate, and potassium silicate; and
   applying said mass to an area where said fire is to be extinguished.

* * * * *

UNITED STATES PATENT AND TRADEMARK OFFICE
CERTIFICATE OF CORRECTION

PATENT NO. : 4,665,993

DATED : May 19, 1987

INVENTOR(S) : Balassa

It is certified that error appears in the above—identified patent and that said Letters Patent are hereby corrected as shown below:

Claim 1, line 1 (col. 5, line 10) change "first" to --fire--.

Signed and Sealed this

Twenty-second Day of December, 1987

Attest:

*Attesting Officer*

DONALD J. QUIGG

*Commissioner of Patents and Trademarks*